United States Patent [19]

Riegel et al.

[11] 3,965,202

[45] June 22, 1976

[54] PRODUCTION OF TRICHLORO-ETHYLENE FROM WASTE $C_2$ CHLORINATED HYDROCARBONS

[75] Inventors: Herbert Riegel, Maplewood; Morgan C. Sze, Upper Montclair; Harvey D. Schindler, Fair Lawn, all of N.J.

[73] Assignee: The Lummus Company, Bloomfield, N.J.

[22] Filed: June 20, 1973

[21] Appl. No.: 371,613

[52] U.S. Cl. .................... 260/654 R; 260/654 H; 260/DIG. 42; 252/415
[51] Int. Cl.² .................................................. C07C 21/04
[58] Field of Search..... 260/654 R, 654 H, DIG. 42; 252/415

[56] References Cited
UNITED STATES PATENTS

| | | | |
|---|---|---|---|
| 2,498,546 | 2/1950 | Gorin | 260/659 |
| 2,577,388 | 12/1951 | Warren | 260/654 H |
| 3,548,016 | 12/1970 | Sze | 260/659 |
| 3,674,881 | 7/1972 | Lukes et al. | 260/654 H |

FOREIGN PATENTS OR APPLICATIONS

| | | | |
|---|---|---|---|
| 530,482 | 9/1956 | Canada | 260/654 H |

*Primary Examiner*—Delbert E. Gantz
*Assistant Examiner*—Joseph A. Boska
*Attorney, Agent, or Firm*—Marn & Jangarathis

[57] ABSTRACT

All or a portion of chlorinated hydrocarbons convertible to trichloroethylene and/or perchloroethylene by chlorination, dehydrochlorination or dehydrogenation and optionally also dechloroination are recovered from a $C_2$ chlorinated hydrocarbon waste stream and contacted with a molten mixture of, for example, cuprous chloride, cupric chloride and copper oxychloride and hydrogen chloride and/or chlorine, to produce an effluent which contains as reaction product trichloroethylene and/or perchloroethylene. Chlorinated components in the waste stream not contacted with the molten mixture can be burned and the chlorine values used to enrich the chlorine content of the melt.

8 Claims, 2 Drawing Figures

PRODUCTION OF TRICHLORO-ETHYLENE FROM WASTE C$_2$ CHLORINATED HYDROCARBONS

The present invention is directed to the treatment of waste streams, and more particularly to the treatment of chlorinated C$_2$ hydrocarbon waste streams. Still more particularly, the present invention is directed to the production of trichloroethylene and/or perchloroethylene from chlorinated C$_2$ hydrocarbon waste streams.

Various chemical operations produce waste streams of chlorinated hydrocarbons. Thus, for example, in the production of vinyl chloride as much as 4–8% of the production is primarily in the form of a waste chlorinated C$_2$ hydrocarbon stream comprised of ethyl chloride, dichlorethylenes, dichloroethanes, trichloroethanes, trichloroethylenes, tetrachloroethanes and heavier chlorinaed C$_2$ hydrocarbons. In general, such waste streams are disposed of by combustion to convert contained chlorine values to hydrogen chloride which can be neutralized or recovered as acid or in anhydrous form.

The above process are generally wasteful in that the chlorine values are not directly utilizable, and all hydrocarbon values are lost.

An object of the present invention is to provide a new and improved process for treating waste streams containing chlorinated C$_2$ hydrocarbons.

Another object of the present invention is to provide a new and improved process for producing valuable products from such waste streams.

A further object of the present invention is to provide a new and improved process for producing trichloroethylene and/or perchloroethylene from waste streams containing chlorinated C$_2$ hydrocarbons.

These and other objects of the present invention will be more readily apparent from reading the following detailed description thereof with reference to the accompanying drawings wherein.

Figure 1:
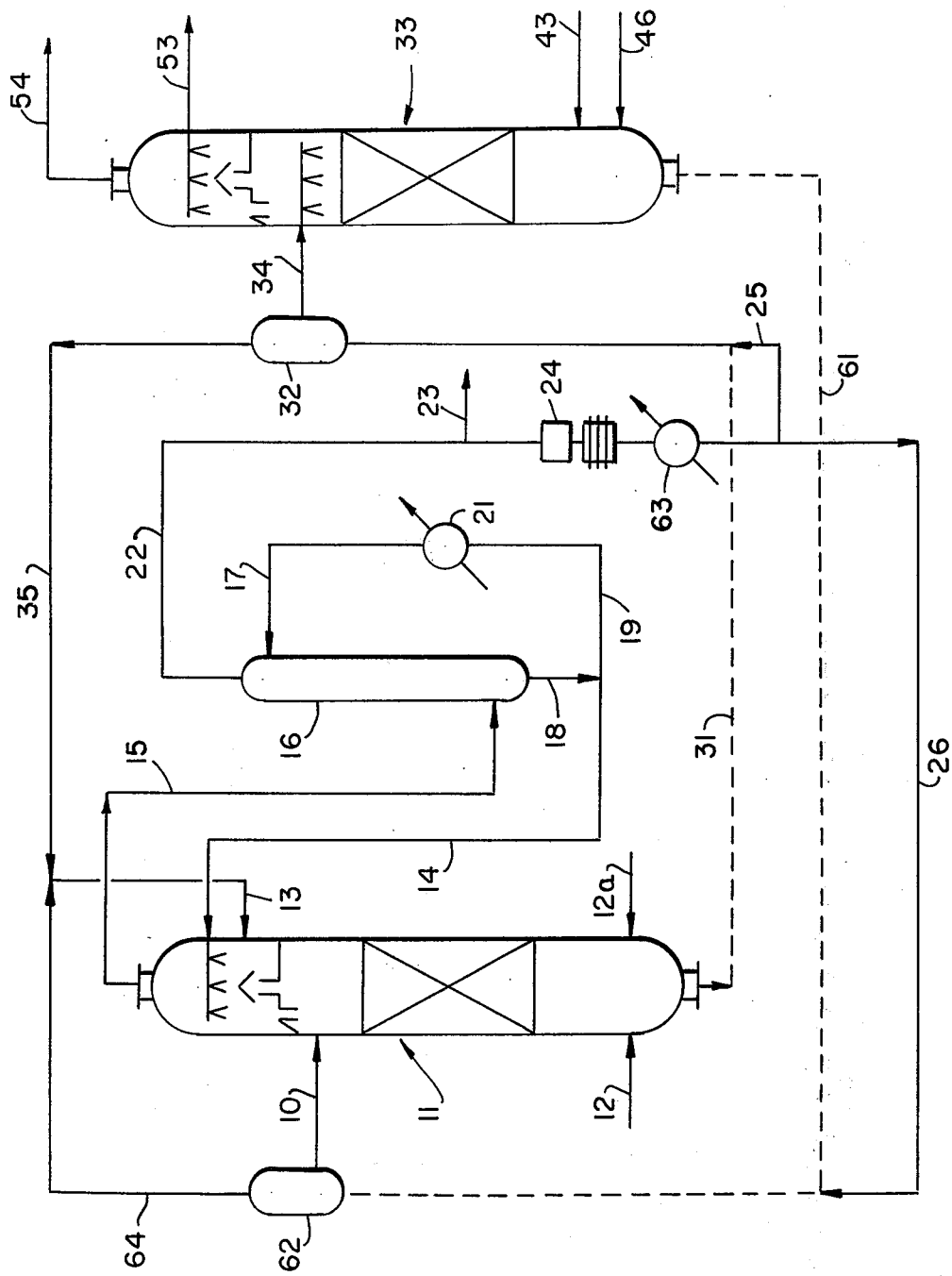
FIG. 1 is a simplified schematic flow diagram of the reaction portion of an embodiment of the present invention.

The objects of the present invention are broadly accomplished, in one aspect, by producing trichloroethylene and/or perchloroethylene from a chlorinated C$_2$ hydrocarbon waste stream. In accordance with the present invention, the chlorinated C$_2$ hydrocarbon waste stream is fractionated to recover chlorinated C$_2$ hydrocarbon components which can be converted to trichloroethylene and/or perchloroethylene. All or a portion of such recovered components are contacted in a chlorination zone with hydrogen chloride, chlorine or a mixture thereof, and a molten mixture of the higher and lower valent chlorides of a multivalent metal and the oxychlorine of the metal to produce a chlorination effluent containing as reaction product trichloroethylene and/or perchloroethylene. The chlorination effluent also includes chlorinated C$_2$ hydrocarbons which can be converted to trichloroethylene, and/or perchloroethylene, with all or a portion of such components being recycled to the chlorination zone.

All or a portion of the chlorinated hydrocarbon components present in the waste stream and chlorination effluent which are not recycled to the chlorination zone can be burned to recover chlorine values therefrom, as chlorine and/or hydrogen chloride. The chlorine values may be recovered from the combustion effluent by contacting the effluent with melt from the chlorination zone, the melt also being contacted with oxygen to generate oxychloride. The melt having increased chlorine values, and containing oxychloride, is recycled to the chlorination zone.

Thus, in accordance with the present invention either trichloroethylene, perchloroethylene or both trichloroethylene and perchloroethylene can be produced, as reaction product, from a chlorinated C$_2$ hydrocarbon waste stream.

The melt contains a chloride of a multivalent metal; i.e., a metal having more than one positive valence state, such as manganese, iron, copper, cobalt, and chromium, preferably copper. In the case of higher melting multivalent metal chlorides, such as copper chlorides, a metal salt melting point depressant which is non-volatile and resistant to the action of oxygen at the process conditions, such as a chloride of a univalent metal, i.e., a metal having having only one positive valence state, is added to the multivalent metal chloride to form a molten salt mixture having a reduced melting point. The univalent metal chlorides, are preferably alkali metal chlorides, such as potassium and lithium chloride in particular, but it is to be understood that other metal chlorides and mixtures thereof, such as the heavy metal chlorides, i.e., heavier than copper, of Groups I, II, III and IV of the Periodic Table; e.g., zinc, silver, and thallium chloride, may also be employed. The metal chloride melting point depressant is added in any amount sufficient to maintain the salt mixture as a melt at the reaction temperatures, and is generally added in amount sufficient to adjust the melting point of the molten salt mixture to a temperature of below and 500°F. In the case of a salt mixture of copper chlorides and potassium chloride, the composition of the melt ranges between about 20% and about 40%, preferably about 30%, by weight, potassium chloride, with the remainder being copper chlorides. It is to be understood, however, that in some cases the catalyst melt may have a melting point higher than 500°F., provided the catalyst remains in the form of the melt throughout the processing steps. It is further to be understood that the melt may contain a mixture of multivalent metal chlorides or other reaction promoters. It is also to be understood that in some cases, metal chloride may be maintained as a melt without the addition of a univalent metal halide.

The chlorinated C$_2$ hydrocarbon waste stream contains waste chlorinated hydrocarbons which are convertible to trichloroethylene and/or perchloroethylene, such components being one or more of the following: monochlorinated C$_2$ hydrocarbons (vinyl chloride and ethyl chloride); dichlorinated C$_2$ hydrocarbons (dichloroethanes and dichloroethylenes); trichlorinated C$_2$ saturated hydrocarbons (trichloroethanes) perchloroethanes, pentachloroethane and hexachloroethane. A waste stream recovered from a typical vinyl chloride plant can contain all of the hereinabove specified components, in various proportions. In accordance with the present invention all or a portion of such components (some of the components may be recovered as separate product, if there is an available market or burned as hereinafter described) are introduced into a chlorination reaction zone (the reaction zone is referred to as a chlorination reaction zone even though dehydrogenation, dehydrochlorination and dechlorination can also be effected therein) for conversion to trichloroethylene and/or perchloroethylene, as partially represented by the following overall equations:

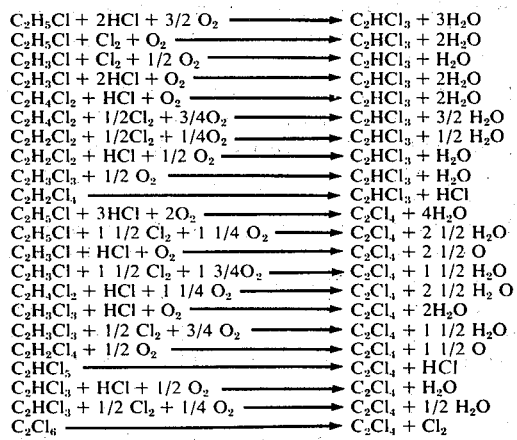

Thus, in the presence of the hereinabove described molten mixture, the waste chlorinated $C_2$ hydrocarbons are either chlorinated, dehydrogenated, dechlorinated or dehydrochlorinated to produce trichloroethylenes and/or perchloroethylenes. The reaction sequence which is effected in the chlorination zone, for a typical chlorination reaction, using trichloroethane and copper chlorides, as representative examples, is believed to be represented by the following equations:

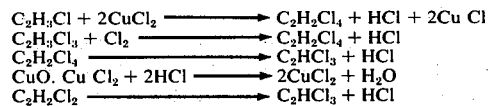

The oxygen requirements for the process are provided by contacting the melt, in a separate oxidation reaction zone, with molecular oxygen, generally in the form of air, as represented by the following equation, using copper chloride, as a representative example:

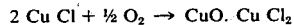

In this manner, the oxygen requirements for the process are provided without direct contact between oxygen and the feed stream.

The chlorination reaction zone is generally operated at a temperature from about 700°F. to about 1200°F., preferably from about 750°F. to about 1000°F., although lower temperatures; e.g., about 575°F., may be employed and at pressures from about 1 to about 20 atmospheres. The feed and melt are generally contacted in a countercurrent fashion, preferably with the feed as a continuous vapor phase, at residence times of from about 1 to about 60 seconds, although longer residence times may be employed. The chlorine and/or hydrogen chloride is generally introduced into the chlorination zone in about stoichiometric proportions in order to essentially eliminate the presence thereof in the effluent (the effluent contains equilibrium amounts of hydrogen chloride.)

The preferred molten salts are the copper chlorides, with the preferred molten mixtures, generally containing from about 20% to about 40%, by weight, potassium chloride as a melting point depressant.

The cupric chloride content of the melt is generally at least about 20% by weight, of the melt, and generally from about 30% to about 40%, by weight, in order to provide sufficient cupric chloride for the various reactions. It is to be understood, however, that lower amounts of cupric chloride may also be employed by increasing reaction temperature and residence time. The molecular oxygen is preferably introduced into the oxidation reaction zone in an amount, and at a rate, to provide a molten salt mixture containing from about 0.5% to about 5.5%, preferably from about 1% to about 1%, all by weight, of copper oxychloride.

The effluent from the chlorination zone contains, in addition to trichloroethylene and/or perchloroethylene, components, as hereinabove described, which are convertible to trichloroethylene and/or perchloroethylene. In accordance with the present invention, such components are recovered from the chlorination effluent, and all, or a portion thereof, are recycled to the chlorination zone for production of further trichloroethylene and/or perchloroethylene.

The waste stream and the chlorination effluent generally also contain chlorinated hydrocarbon components which are not converted to trichloroethylene and/or perchloroethylene, such components in the case where only trichloroethylenes are desired as reaction product being chlorinated $C_2$ hydrocarbons heavier than perchloroethanes (the term "heavier" means that the component has a boiling temperature which is higher than the boiling temperature of the perchloroethanes), such as pentachloroethane, hexachloroethane and chlorinated hydrocarbons containing more than two carbon atoms, and in accordance with the present invention, all or a portion of such heavier chlorinated $C_2$ hydrocarbon components (some of such heavier components may be recovered as byproduct if there is an available market) are burned to recover the chlorine values therefrom, as chlorine and/or hydrogen chloride. In the case where, perchloroethylene, is desired as reaction product, chlorinated hydrocarbons containing more than two carbon atoms can be burned to recover chlorine values. It is also to be understood, that in some cases, when present in small amounts, components which could be converted to trichloroethylene and/or perchloroethylene can be burned instead of being recovered and recycled to the chlorination zone. The combustion may be effected over a wide range of conditions, with the combustion temperature generally being from about 1000°F. to about 3000°F. and the pressure generally being from about 1 to 30 atmospheres. The molecular oxygen requirements for the combustion are generally provided as air with the oxygen generally being present in an amount to provide at least one mole of oxygen per atom of carbon and one quarter mole per atom of hydrogen. In some cases, in order to maintain the desired combustion conditions, fuel is added to the combustion feed, and in such cases, sufficient oxygen must be present to meet the oxygen requirements of the fuel. The combustion effluent, includes in addition to hydrogen chloride and/or chlorine, water vapor, carbon oxide (carbon monoxide and/or carbon dioxide) and nitrogen is then treated to recover the chlorine values.

It should be readily apparent that the above conditions are only illustrative and that optimum conditions will vary, with the choice of such optimum conditions being within the scope of those skilled in the art from the teachings herein.

The chlorine and/or hydrogen chloride are recovered from the combustion effluent in the oxidation reaction zone by contacting the effluent and a molecular oxygen-containing gas with a melt containing a multivalent metal chloride in both the higher and lower valence state, with the various reactions, using copper as a representative multivalent metal, being represented by the following equations:

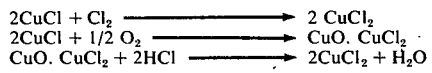

$$2CuCl + Cl_2 \longrightarrow 2\,CuCl_2$$
$$2CuCl + 1/2\,O_2 \longrightarrow CuO \cdot CuCl_2$$
$$CuO \cdot CuCl_2 + 2HCl \longrightarrow 2CuCl_2 + H_2O$$

The contacting of the combustion effluent with the melt and the oxygen-containing gas results in selective absorption of the chlorine and/or hydrogen chloride from the combustion effluent, resulting in an increase in the chlorine value of the melt; i.e., the melt is enriched in cupric chloride.

The contacting in the oxidation reaction zone is generally effected at temperatures from about 600°F. to about 900°F. (although higher temperatures may be employed; e.g., up to about 1200°F., but are generally not preferred as a result of poor oxygen absorption by the melt), pressures from about 1 to about 20 atmospheres and residence times from about 1 to about 60 seconds, although longer residence times may also be employed. The contacting is preferably effected in a countercurrent fashion with the combustion effluent and oxygen-containing gas as a continuous vapor phase.

The oxygen requirements for absorbing the hydrogen chloride from the melt may be supplied to the reaction from either an external source or by effecting the combustion of the chlorinated hydrocarbons with an excess of oxygen, whereby the molecular oxygen for the reaction is provided with the combustion effluent. The melt from the oxidation reaction zone is to be employed in the chlorination reaction zone and, therefore, as hereinabove described, the melt withdrawn from the third reaction zone also contains oxychloride. Therefore, the oxygen provided to the oxidation reaction zone is in an amount sufficient to effect both recover of the hydrogen chloride from the combustion effluent and provide a net production of oxychloride for use in the chlorination reactor.

It should be apparent from the hereinabove noted reaction sequences, that the melt containing the multivalent metal chloride, in some cases, participates in the reaction sequence and accordingly does not behave only as a catalyst. Thus, for example, the melt functions to transfer oxygen, and as should be apparent from the hereinabove noted equations, sufficient oxychloride must be produced to provide the oxygen requirements for the reaction, such requirements being greater for hydrogen chloride as compared to chlorine.

The melt, in addition to functioning as a reactant and/or catalyst is a temperature regulator. Thus, the circulating melt has a high heat absorption capacity thereby preventing runaway reaction during the exothermic chlorination and oxygen contacting steps. The absorbed heat of reaction may be employed to both heat the various reactants to reaction temperature and supply heat for the endothermic dehydrochlorination. It should be apparent, however, that if additional heating or cooling is required, such heating or cooling may be supplied from an external source.

In accordance with one embodiment of the invention, only trichloroethylenes are recovered as reaction product. In such an embodiment, perchloroethylene and chlorinated components heavier than tetrachloroethane can be burned to recover chlorine values therefrom.

In accordance with another embodiment, trichloroethylene and perchloroethylene can be recovered as reaction product, in which case, the remaining chlorinated $C_2$ hydrocarbons heavier than tetrachloroethane can be recycled for conversion to the aforesaid products or burned.

In accordance with a further embodiment, only perchloroethylene can be recovered, as reaction product, in which case trichloroethylene is also recycled for ultimate conversion to perchloroethylene.

In accordance with still another embodiment, 1,1,1-trichloroethane can also be recovered as a reaction product from both the waste stream and effluent from the chlorination zone.

In accordance with yet a further embodiment, ethane and/or ethylene may be added, as fresh feed, to the chlorination zone for production of trichloroethylene and any other additional chlorinated $C_2$ hydrocarbons, such as 1,1,1-trichloroethane and/or perchloroethylene which are to be recovered as product.

Thus, as should be apparent from the hereinabove description, a waste stream, containing chlorinated $C_2$ hydrocarbons can be effectively utilized to produce trichloroethylene, and in some cases, other valuable products. In accordance with the present invention essentially all chlorine values and hydrocarbon values present in the waste stream are converted to valuable product.

The invention will now be further described with reference to embodiments thereof illustrated in the accompanying drawings. It is to be understood, however, that the scope of the invention is not to be limited thereby. It is further to be understood that the molten copper chloride salts are highly corrosive and, accordingly, the processing equipment must be suitably protected; e.g., the reactors may be lined with ceramic. Similarly, if pumps are used for transporting the molten salts they may also be protected. The molten salts, however, are preferably transferred between the reactors by the use of gas lifts, as known in the art.

Referring now to FIG. 1, a molten chloride salt, such as a mixture of potassium chloride, cuprous chloride and cupric chloride in line 10 is introduced into the top of the reaction portion of an oxidation vessel 11 maintained, as hereinabove described, at temperatures and pressures suitable for oxidizing the molten salt. A combustion effluent in line 12a, obtained as hereinafter described, containing hydrogen chloride and chlorine, carbon oxide, water vapor, nitrogen and optionally also molecular oxygen is introduced into vessel 11. A compressed oxygen-containing gas, such as air, if required (in the event that the combustion effluent does not include sufficient oxygen), in line 12 is introduced into the bottom of vessel 11 and is passed along with the combustion effluent in countercurrent contact to the descending molten salt, resulting in oxidation of the salt to produce copper oxychloride with the concurrent evolution of heat, and recovery of the hydrogen chloride and chorine from the combustion effluent, resulting in a net increase in the cupric chloride content of the melt.

An effluent gas, essentially free of chlorine and/or hydrogen chloride (the gas contains equilibrium amounts thereof) rises into the top of vessel 11 wherein the effluent gas is combined with lift gas, as hereinafter described, introduced through line 13. The effluent gas is directly contacted in the top of vessel 11 with a spray of quench liquid, in particular aqueous hydrogen chloride introduced through line 14 to cool the effluent gas and thereby eliminate any vaporized and entrained salts therefrom. The effluent gas, now containing vaporized quench liquid, is withdrawn from vessel 11 through line 15 and introduced into a direct contact quench tower 16, of a type known in the art wherein the effluent gas is cooled by direct contact with a suitable quench liquid, in particular aqueous hydrogen chloride, introduced through line 17 to thereby remove vaporized quench liquid from the effluent gas.

The quench liquid is withdrawn from the bottom of tower 16 through line 18 and a first portion passed through line 14 for quenching the effluent gas in vessel 11. A second portion of the quench liquid is passed through line 19, containing a cooler 21, for introduction into the quench tower is 16 through line 17.

An effluent gas, is withdrawn from quench tower 16 through line 22 and a portion thereof purged through line 23. The remaining portion of the effluent gas is compressed in compressor 24 and the temperature thereof regulated in heat exchanger 63 prior to passage through lines 25 and 26 for use as a lift gas for transporting molten salt, as hereinafter described.

The molten salt, now containing copper oxychloride, is withdrawn from the bottom of vessel 11 through line 31 and lifted by the lift gas in line 25 into a separation vessel 32 positioned adjacent the top of the reaction portion of a reaction vessel 33. In separator 32, the molten salt is separated from the lift gas, with the separated lift gas being withdrawn through line 35 and combined with lift gas from the oxidation reactor for introduction into the quenching portion of vessel 11 through line 13.

The molten salt, containing cuprous chloride, cupric chloride, copper oxychloride and the potassium chloride melting point depressant, from separator 32, in line 34, is introduced into reaction vessel 33.

Fresh feed chlorine and/or hydrogen chloride is introduced into the bottom of reaction vessel 33 through line 43. A chlorinated $C_2$ hydrocarbon feed preferably comprised of one or more of the following components; monochlorinated $C_2$ hydrocarbons, dichlorinated $C_2$ hydrocarbons, trichlorinated $C_2$ saturated hydrocarbons and tetrachloroethanes, is introduced into reaction vessel 33 through line 46. The chlorinated $C_2$ hydrocarbon feed is comprised of fresh feed recovered from a waste stream, and recycle components, as hereinafter described.

The reaction vessel 33 is operated at the conditions hereinabove described to effect dehydrogenation, chlorination and dehydrochlorination of the various chlorinated $C_2$ hydrocarbon components to produce trichloroethylene.

An effluent containing trichloroethylene, and in addition, monochlorinated $C_2$ hydrocarbons, dichlorinated $C_2$ hydrocarbons, trichlorinated, ethanes, perchloroethylene, perchlorinated ethanes, chlorinated $C_2$ hydrocarbons heavier than perchlorinated ethanes, water vapor and some hydrogen chloride (generally equilibrium amounts) is directly contacted in the top of vessel 33 with a spray of quench liquid, in particular one or more of the chlorinated hydrocarbons produced in the reaction vessel 33, introduced through line 53 to cool the effluent gas and thereby eliminate vaporized and entrained salts therefrom.

The effluent gas, now containing vaporized quench liquid, is withdrawn from vessel 33 through line 54 and introduced into a separation and recovery section (FIG. 2) for recovery of the various components.

A molten salt is withdrawn from the bottom of reactor 33 through line 61 and lifted by lift gas in line 26 into a separation vessel 62 positioned adjacent the tope of reactor 11. In separator 62, the molten salt is separated from the lift gas and introduced through line 10 into vessel 11. The lift gas is withdrawn from separator 62 through line 64 and combined with the lift gas in line 35 for introduction into the top quenching section of vessel 11 through line 13.

Figure 2:
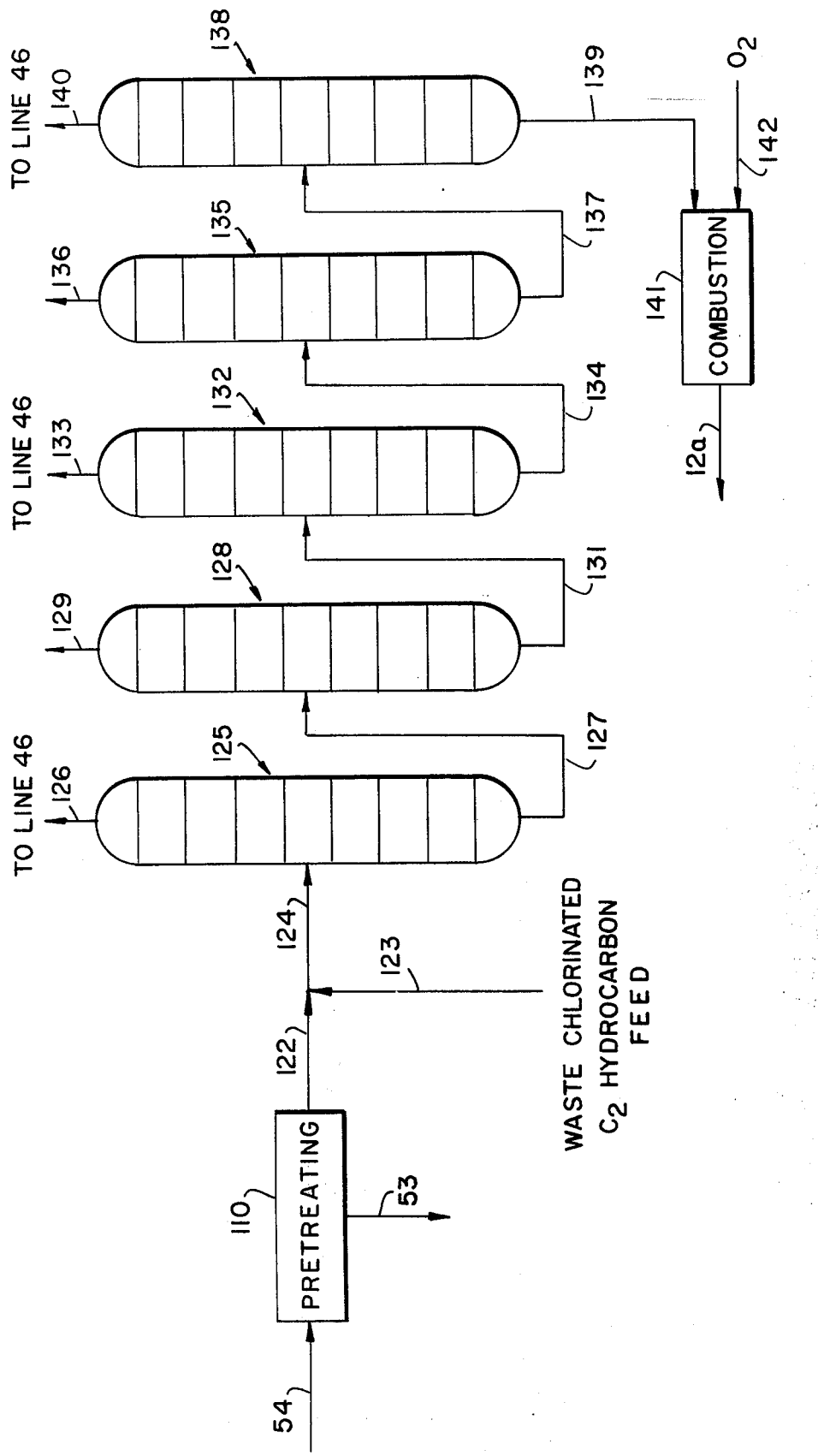
FIG. 2 is a simplified schematic flow diagram of the recovery section of the embodiment of FIG. 1.

Referring now to FIG. 2, the reaction effluent in line 54 is introduced into pretreating zone 110 to separate water and hydrogen chloride therefrom, as known in the art. In addition, chlorinated hydrocarbon to be used as quench liquid is recovered therefrom and recycled through line 53.

A dried chlorinated hydrocarbon stream in line 122 is combined with a waste stream, containing chlorinated $C_2$ hydrocarbons as net feed in line 123. The waste stream in line 123, as hereinabove described, contains one or more of the following components: mono-, di-, tri-, tetra, penta- and hexa-chlorinated $C_2$ hydrocarbons, and generally a mixture of all such components.

The combined stream in line 124 is introduced into a fractional distillation column 125 operated at temperatures and pressures to recover, as overhead, components lighter than trichloroethylene in particular one or more of the following: monochlorinated $C_2$ hydrocarbons, dichlorinated $C_2$ hydrocarbons and 1,1,1-trichloroethane. The overhead is withdrawn from column 125 through line 126 and recycled to reactor 33 through line 46.

A bottoms comprised of trichloroethylene and heavier components is withdrawn from column 125 through line 127 and introduced into fractional distillation column 128 operated at a temperature and pressure to recover trichloroethylene as overhead. Trichloroethylene is withdrawn as net reaction product from column 128 through line 129.

A bottoms comprised of components heavier than trichloroethylene is withdrawn from column 128 through line 131 and introduced into fractional distillation column 132 designed and operated to recover components lighter than perchloroethylene as overhead, in particular 1,1,2-trichloroethane. An overhead of components lighter than perchloroethylene is withdrawn from column 132 through line 133 and recycled to reactor 33 through line 46.

A bottoms comprised of perchloroethylene and heavier components, in particular perchloroethylene, tetrachloroethanes chlorinated $C_2$ hydrocarbons containing 5 or more chlorine atoms and chlorinated hydrocarbons containing more than two carbon atoms, if present, is withdrawn from column 132 through line 134. The bottoms stream contains components which are potentially convertible to trichloroethylene, namely perchloroethylene, tetrachloroethanes, pentachloroethane and hexachloroethane. The utilization of this bottoms stream is dependent on the economics of recovering the various components.

In accordance with a preferred procedure wherein perchloroethylene is to be recovered as reaction product, the bottoms in line 134 is introduced into a fractional distillation column 135 designed and operated to recover perchloroethylene as overhead. A overhead comprised of perchloroethylene is withdrawn, as reaction product, from column 135 through line 136.

A bottoms, comprised of components heavier than perchloroethylene is withdrawn from column 135 through line 137 and introduced into fractional distillation column 138 designed and operated to recover tetrachloroethanes as overhead. The tetrachloroethane overhead recovered in line 139 is recycled to reactor 33 through line 46.

A bottoms comprised of components heavier than tetrachloroethanes is withdrawn from column 138 through line 139 and introduced into a combustion zone 141 along with an oxygen containing gas in line 142 to effect combustion, as hereinabove described. A combustion effluent containing hydrogen chloride and chlorine is withdrawn through line 12a and introduced into reactor 11, as hereinabove described, to recover chlorine values therefrom.

It is to be understood that in the case where perchloroethylene is not desired as reaction product, and tetrachloroethane is not present in an amount to economically justify recovery thereof, the bottoms in line 134 may be passed directly to the combustion zone. Similarly, in the case where perchloroethylene is recovered as product and tetrachloroethane is not present in amounts to justify recovery thereof, the bottoms in line 137 may be passed to the combustion zone.

It is also to be understood that the chlorinated $C_2$ hydrocarbons heavier than 1,1,2-trichlorinated ethane in addition to tetrachloroethanes i.e., perchloroethylene, penta- and hexa-chloroethanes are also potentially convertible to trichloroethylene and, accordingly, one or more of such components could, in some cases, be recycled to reactor 33.

Numerous modifications and variations of the hereinabove described embodiment are possible within the spirit and scope of the present invention. Thus, for example, a separate recovery section could be provided for the waste stream and the chlorination effluent instead of combining the two streams as particularly described.

As a further modification ethane and/or ethylene may be introduced as fresh feed into the chlorination zone. In such a modification, the recycle stream will also contain ethane and/or ethylene.

As a further modification, 1,1,1-trichloroethane can be recovered as co-reaction product. In such a modification, column 125 is operated to recover components lighter than 1,1,1-trichloroethane, as overhead product and an additional column is required to separate 1,1,1-trichloroethane, as overhead, from trichloroethylene and heavier components.

As yet a further modification, perchloroethylene can be recovered as sole reaction product. In such an embodiment, towers 128 and 132 can be eliminated and tower 125 is designed and operated to recover components lighter than perchloroethylene, as overhead, for recycle to reactor 33. The bottoms from tower 125 is introduced into tower 135 whereinn perchloroethylene is recovered, as overhead product. The bottoms from tower 135 may either be burned or introduced into tower 138 to recover tetrachloroethanes and additionally, if economically justified, pentachloroethanes and hexachloroethanes for recycle to reactor 33. The remaining chlorinated hydrocarbons may then be combusted to recover chlorine values, as hereinabove described.

The above modifications and others should be apparent to those skilled in the art from the teachings herein.

The present invention is particularly advantageous in that chlorinated $C_2$ hydrocarbon waste streams, such as those produced in conventional processes for producing vinyl chloride, can be utilized for the production of valuable products while minimizing loss of chlorine and hydrocarbon values.

In accordance with the preferred procedure trichloroethylene and perchloroethylene are recovered as net products with tetrachloroethane and chlorinated $C_2$ hydrocarbons lighter than perchlorinated ethylene, present in the waste stream and chlorination effluent, being recycled to the chlorination zone, and chlorinated hydrocarbons heavier than tetrachlorinated ethanes being combusted for recovering of chlorine values, as hereinabove described.

Numerous modifications and variations of the present invention are possible in light of the above teachings and, therefore, within the scope of the appended claims, the invention may be practised otherwise than as particularly described.

What is claimed:

1. A process for producing a chlorination product selected from the group consisting of trichloroethylene, perchlorethylene and mixtures thereof, comprising:
   a. introducing into a separation zone a waste $C_2$ chlorinated hydrocarbon stream derived from the production of vinyl chloride containing said chlorination product and a plurality of $C_2$ chlorinated hydrocarbons convertible to said chlorination product selected from the group consisting of monochlorinated $C_2$ hydrocarbons, dichlorinated $C_2$ hydrocarbons, trichloroethanes, perchloroethanes and pentachloroethane;
   b. recovering from the waste stream in said separation zone said chlorination product and said plurality of $C_2$ chlorinated hydrocarbons convertible to said chlorination product;
   c. contacting said plurality of $C_2$ chlorinated hydrocarbons with a molten mixture comprising the higher and lower valent chlorides of a multivalent metal and the oxychloride of the metal and a chlorinating agent selected from the group consisting of hydrogen chloride, chlorine and mixtures thereof, said contacting being effected at a temperature of from 700°F to 1200°F to produce a reaction effluent containing said chlorination product and plurality of $C_2$ chlorinated hydrocarbon by-products convertible to said chlorination product selected from the group consisting of monochlorinated $C_2$ hydrocarbons, dichlorinated $C_2$ hydrocarbons, trichloroethanes, perchloroethanes and pentachloroethane;
   d. recovering said by-products and said chlorination product; and
   recycling the by-products to step (c).

2. The process of claim 1 wherein said plurality of $C_2$ chlorinated hydrocarbons convertible to said chlorination product which are passed to step (c) are lighter than perchloroethylene.

3. The process of claim 2 wherein the molten mixture comprises cuprous chloride, cupric chloride and copper oxychloride.

4. The process of claim 3 wherein a member selected from the group consisting of ethylene, ethane and mixtures thereof is employed in step (c).

5. The process of claim 4 wherein trichloroethylene is recovered as said chlorination product.

6. A process for producing as a chlorinated reaction product trichloroethylene and perchloroethylene, comprising:
   a. combining a waste stream derived from a process for producing vinyl chloride containing said chlorinated reaction product, chlorinated hydrocarbons hevier than tetrahchloroethane and a plurality of chlorinated $C_2$ hydrocarbons ligher than pentachloroethane selected from the group consisting of monochlorinated $C_2$ hydrocarbons, dichlorinated $C_2$ hydrocarbons, trichloroethanes and perchloroethanes, with $C_2$ chlorinated hydrocarbon containing effluent produced in step (c) to produce a combined stream;
   b. separating from said combined stream said chlorinated product, a plurality of $C_2$ chlorinated hydrocarbons lighter than pentachloroethane and chlorinated hydrocarbons heavier than tetrachloroethane;
   c. contacting in a first reaction zone at a temperature of from 700°F t 1200°F said separated plurality of chlorinated $C_2$ hydrocarbons lighter than pentachloroethane with a molten mixture comprising cuprous chloride, cupric chloride and copper oxychloride and a member selected from the group consisting of chlorine, hydrogen chloride and mixtures thereof to produce a $C_2$ chlorinated hydrocarbon containing effluent, containing said chlorinated reaction product, chlorinated hydrocarbons heavier than tetrachloroethane and $C_2$ chlorinated hydrocarbons lighter than pentachloroethane selected from group consisting of monochlorinated $C_2$ hydrocarbons, dichlorinated $C_2$ hydrocarbons, trichloroethanes and perchloroethanes;
   d. employing $C_2$ chlorinated hydrocarbon containing effluent in step (a);
   e. combusting said recovered chlorinated hydrocarbons heavier than tetrachloroethane to produce a combustion effluent containing chlorine and hydrogen chloride;
   f. contacting, in a second reaction zone, the combustion effluent with molecular oxygen and a molten mixture from the first reaction zone to recover hydrogen chloride and chlorine from the combustion effluent by enriching the melt in cupric chloride and to produce copper oxychloride; and
   g. passing melt from the second reaction zone to the first reaction zone.

7. The process of claim 6 wherein a member selected from the group consisting of ethane, ethylene and mixtures thereof is introduced into the first reaction zone.

8. The process of claim 6 wherein the recovery in step (b) is effected by introducing the combined stream into a first fractional distillation zone to recover components lighter than trichloroethylene, as overhead, which are passed to step (c); bottoms from the first fractional distillation zone being introduced into a second fractional distillation zone to recover trichloroethylene as overhead chlorinated reaction product; bottoms from the second fractional distillation zone being introduced into a third fractional distillation zone to recover trichloroethane as overhead which is passed to step (c); bottoms from the third fractional distillation zone being introduced into a fourth fractional distillation zone to recover perchloroethylene as overhead chlorinated reaction product; and introducing bottoms from the fourth fractional distillation zone into a fifth fractional distillation zone to recover tetrachloroethane as overhead which is recycled to step (c) and, as bottoms, said chlorinated hydrocarbons heavier than tetrachloroethane.

* * * * *

UNITED STATES PATENT OFFICE
CERTIFICATE OF CORRECTION

Patent No. 3,965,202          Dated June 22, 1976

Inventor(s) Herbert Riegel et al.

It is certified that error appears in the above-identified patent and that said Letters Patent are hereby corrected as shown below:

In the Abstract:
Line 4, "dechloroination" should be -- dechlorination --.

In the Specification:
Column 1, line 20, "chlorinaed" should be -- chlorinated --;
          line 59, "oxychlorine" should be -- oxychloride --.
Column 2, line 37, "and" should be -- about --.
Column 4, line 12, "1%" should be -- 3% --;
          line 54, insert -- about -- after "least".
Column 5, line 44, "recover" should be -- recovery --.
Column 6, line 45, "may" should be -- must --.
Column 7, line 23, delete "is".
Column 8, line 11, "tope" should be -- top --.
Column 9, line 5, "A" should be -- An --;
          line 13, "139" should be -- 140 --;
          line 64, "whereinn" should be -- wherein --.

In the Claims:

Column 11, Claim 6, line 12, "tetrahchloroethane" should be -- tetrachloroethane --;

Claim 6, line 27, "t" should be -- to --.

Signed and Sealed this

Twenty-fifth Day of January 1977

[SEAL]

Attest:

RUTH C. MASON
Attesting Officer

C. MARSHALL DANN
Commissioner of Patents and Trademarks